US011266492B2

(12) United States Patent
Hoopes (10) Patent No.: US 11,266,492 B2
(45) Date of Patent: Mar. 8, 2022

(54) TENSION TO COMPRESSION TENDON FIXATION

(71) Applicant: Daniel M Hoopes, Orem, UT (US)

(72) Inventor: Daniel M Hoopes, Orem, UT (US)

( * ) Notice: Subject to any disclaimer, the term of this patent is extended or adjusted under 35 U.S.C. 154(b) by 23 days.

(21) Appl. No.: 16/539,209

(22) Filed: Aug. 13, 2019

(65) Prior Publication Data

US 2020/0246131 A1 Aug. 6, 2020

Related U.S. Application Data

(60) Provisional application No. 62/800,497, filed on Feb. 2, 2019.

(51) Int. Cl.
*A61F 2/08* (2006.01)

(52) U.S. Cl.
CPC .......... *A61F 2/0811* (2013.01); *A61F 2/0805* (2013.01); *A61F 2002/0841* (2013.01); *A61F 2002/0852* (2013.01); *A61F 2002/0882* (2013.01)

(58) Field of Classification Search
CPC combination set(s) only.
See application file for complete search history.

(56) References Cited

U.S. PATENT DOCUMENTS

| 5,464,407 | A | 11/1995 | McGuire |
| 5,681,333 | A | 10/1997 | Burkhart et al. |
| 5,891,150 | A | 4/1999 | Chan |
| 7,569,059 | B2 | 8/2009 | Cerundolo |
| 7,572,275 | B2 | 8/2009 | Fallin et al. |
| 9,211,119 | B2 | 12/2015 | Hendricksen et al. |
| 2005/0043805 | A1* | 2/2005 | Chudik ............. A61B 17/1684 623/19.14 |
| 2005/0222619 | A1* | 10/2005 | Dreyfuss ............. A61B 17/0401 606/232 |
| 2010/0228254 | A1* | 9/2010 | Pandya .............. A61B 17/1684 606/80 |
| 2011/0022087 | A1 | 1/2011 | Cerundolo |
| 2013/0123840 | A1* | 5/2013 | Murphy ............. A61B 17/0469 606/228 |
| 2016/0174966 | A1* | 6/2016 | Djurovic ............ A61B 17/0469 606/146 |
| 2016/0213370 | A1* | 7/2016 | Chan ..................... A61F 2/0811 |
| 2017/0202584 | A1 | 7/2017 | Hientzsch et al. |
| 2018/0271514 | A1 | 9/2018 | Burkhart |

* cited by examiner

*Primary Examiner* — Yashita Sharma
(74) *Attorney, Agent, or Firm* — Amy Fiene PC (57) ABSTRACT

A surgical kit for tendon fixation on a bone comprises a working end for passing suture through a bone tunnel and a cannulated device for housing the suture within a channel to provide a dynamic suture fixation that yields a compressive force on the bone over the tendon fixation region.

9 Claims, 12 Drawing Sheets

TENSION TO COMPRESSION TENDON FIXATION

BACKGROUND

Surgery is frequently required to re-attach a torn or separated tendon to the bone to which the tendon would normally be attached. Shoulder rotator cuff injuries, for example, typically involve damage to the rotator cuff tendon such that the tendon or a portion thereof requires reattachment to the humerus. Such damage may be repaired by re-attaching the rotator cuff tendon to the humerus by a suture fixation so that the body's normal healing processes can naturally effect re-attachment of the tendon to the bone. Broadly speaking, suture fixation has many applications for securing one body portion relative to another or relative to a surgical implant, or other device.

BRIEF DESCRIPTION OF DRAWINGS

The following figures represent examples according to principles discussed herein.

DETAILED DESCRIPTION

The following describes one or more improvements to a suture configuration, and particularly, a tendon fixation that translates tension to compression on bone.

Tendons are often fixated with suture at one or more fixation points which causes the tendon at that fixation point to be under tension. Because tendon has a tendency to pull away from bone when under tension, only parts of the tendon at the fixation points (i.e. over anchors, etc.) remain in direct contact with the bone. This has led to many attempts to increase the number of fixation points by using a plurality of attachment points, for example, by using "double row repairs."

By changing the fixation construct to provide dynamic fixation, one can change the paradigm so that the fixation provides a deforming force in favor of healing a tendon.

An example surgical kit for a tendon fixation comprises (1) a working end that includes an elongate element that is dimensioned to be inserted into an anchor hole of a bone tunnel. At the distal end of the elongate element is a blunt, rounded tip to direct suture passing underneath the working end to be guided around a corner of a bone tunnel; and (2) a cannulated device that comprises an elongate member to be inserted into the anchor hole of the bone tunnel, and a channel within the elongate member to receive the suture and slidably maintain the suture. Free ends of the suture are to pass through a primary hole and the anchor hole of the bone tunnel and be secured at fixation points of the tendon and thereby translate tensile forces in the tendon to compression forces on the bone.

An example method of forming a tendon fixation includes forming a bone tunnel that has a corner or a curved portion. A working end is inserted within an anchor hole of the bone tunnel. Suture is passed by the working end and through the bone tunnel. A cannulated device is inserted within an anchor hole of the bone tunnel and suture is received within a channel of the cannulated device. Free ends of the suture that extend from openings of the bone tunnel are stitched at fixation points to provide a dynamic suture fixation that yields a compressive force on the bone.

A standard Mason-Allen fixation includes a tendon-grasping stitch placed on tendon whose attachment was damaged. The tendon is attached to bone in a manner that encourages healing. A suture loop is sewn by a first stitch or fixation located perpendicularly to an injured tendon site followed by a second stitch or fixation that anchors the first stitch and pulls the injured tendon site towards its site of original insertion to a bone. One or more fixation devices are commonly used to anchor suture to bone, however suture can be statically fixed in various ways.

Figure 1:
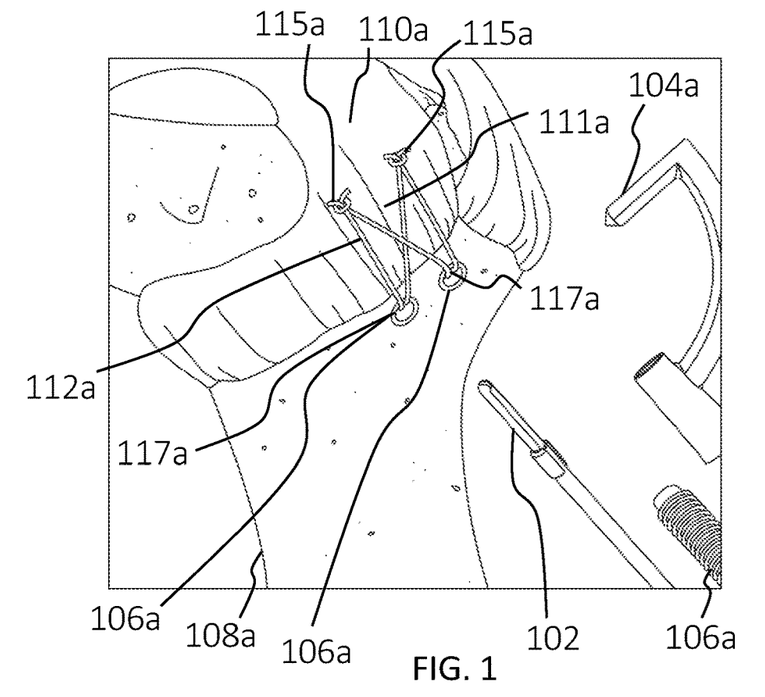
FIG. 1 illustrates a modified Mason-Allen fixation and a surgical kit where suture is passed through a channel of a cannulated device to create a dynamic construct.
Figure 2:
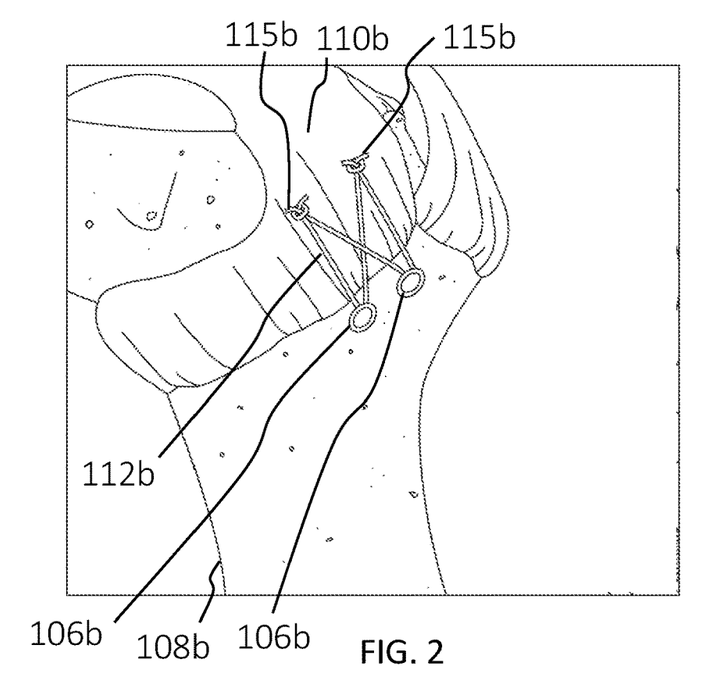
FIG. 2 illustrates a typical Mason-Allen fixation where suture is fixated between the bone and the threads of a cannulated device to create a static construct.

FIGS. 1 and 2 show variations of a Mason-Allen fixation. FIG. 1 illustrates an exemplary new type of Mason-Allen fixation that allows suture to be dynamically positioned within a fixation device 106a. A typical tendon-grasping stitch is modified to allow the suture 112 to be dynamic and not static so as to provide a dynamic fixation. This suture configuration allows compressive tendon 110 forces on bone 108a and thus supports healing of tendon 110. This type of construct establishes a new paradigm where there would normally be a dynamic relationship between tensile forces attempting to pull tendon away from bone but instead the tensile forces are converted to compressive forces on bone.

Particularly, a first free end portion of suture is tied to a proximal portion of a tendon at fixation point 115a. A main portion of suture is passed through a channel within a cannulated device 106a. A second free end portion of suture exits the bone tunnel to be tied to a second proximal portion of the tendon at fixation point 115a. The region bounded between the two tied fixation points 115a and the insertion points 117a of cannulated devices 106a is such that a tensile force on the tendon communicates a compressive force through the suture, the suture having a dynamic sliding engagement to the cannulated devices 106a. The compressive forces are introduced mainly in the region of tendon 111a that is bounded by fixation points 115a and insertion points 117a. The tendon region is hereinafter referred to as the tension-to-compression region ("TTC region") 111a.

In contrast to the new technique, the standard Mason Allen fixation commonly known in the art involves suture fixation configurations that are static, or in other words, there is no movement once the sutures are secured. An exemplary commonly known Mason Allen fixation is shown in FIG. 2. Fixation devices 106b are inserted into the bone 108b and the suture 112b is immovably secured to the fixation devices 106b or secured between the fixation devices 106b and the bone 108b.

Note that the tendon 110b pulls at all points of fixation and the only things resisting failure of the construct are the points of fixation 115b and 106b offered by anchors or bone tunnels. This has led to strategies that increase the number of fixation points to mitigate the problem. Multiple fixation points, either by stitches or fixation devices make it so the stitches are firmly anchored within the tendon and resist tearing through the tendon, however they complicate the procedure and do not alleviate the tension on bone.

The advantage of having a suture be dynamically engaged as shown in FIG. 1 is that it converts tensile forces that would otherwise be acting to pull the tendon away from the bone that are causing failure to instead encourage compressive forces against bone which is better for a healing environment. Various other tendon grasping stitches with fixation points are anticipated to be used according to principles discussed herein, such as Krackow stitch, Massive Cuff stitch, and Ulsan University stitch, etc.

Figure 14:
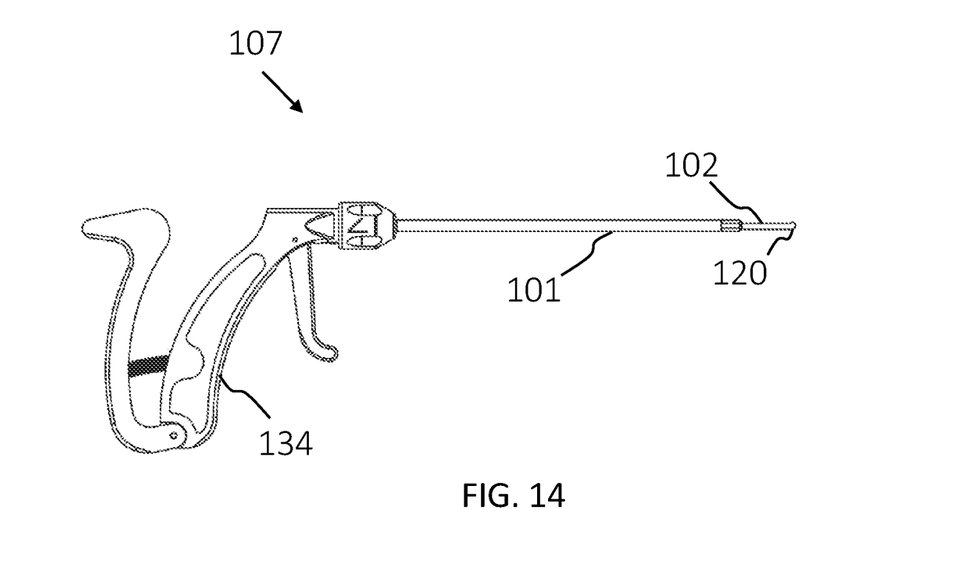
FIG. 14 illustrates a side view of a suture passer.
Figure 15:
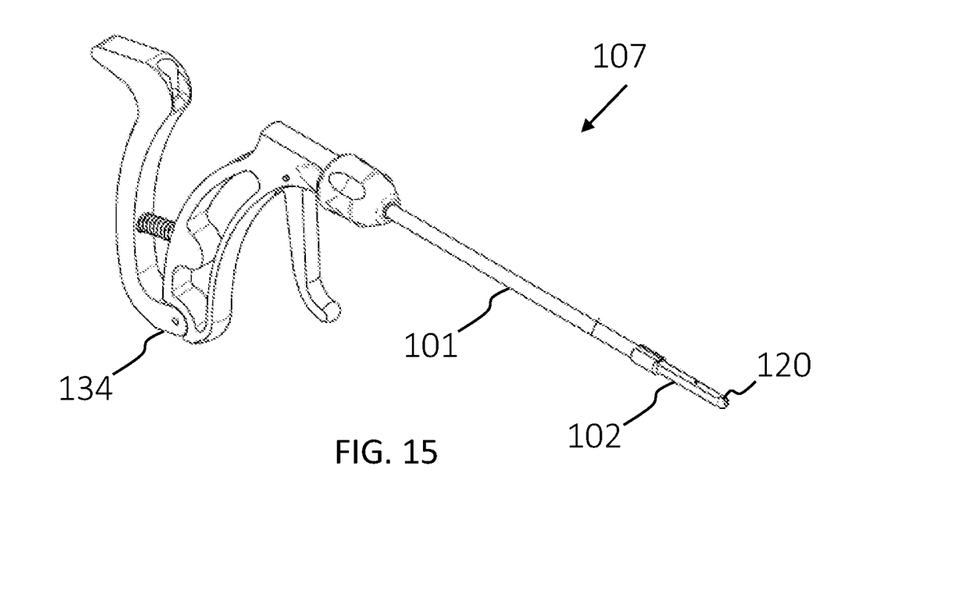
FIG. 15 illustrates a perspective view of a suture passer.

The procedure in FIG. 1 is accomplished with a surgical kit comprising one or more of a drill guide 104, a cannulated device 106, and a working end 102 of a suture passer 107 (see FIGS. 14 and 15). The surgical instruments will be described along with a method for using them in a medical procedure.

Figure 3:
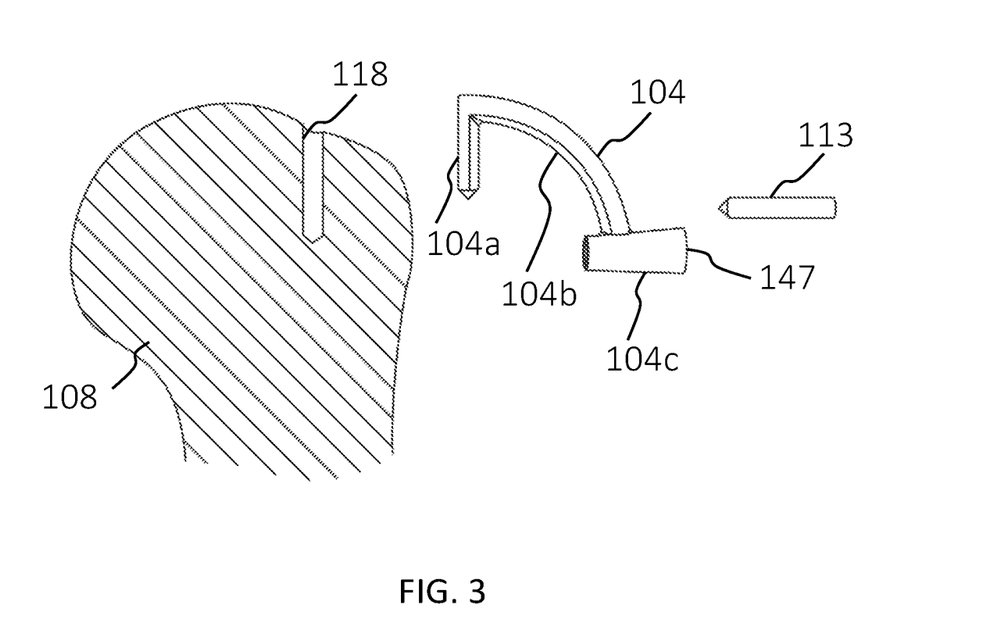
FIG. 3 illustrates a cross-sectional view of a bone, drill guide, and drill bit for creating a bone tunnel from converging holes.

Turning to FIG. 3, the drill guide 104 is shown centered between a bone 108 and an anchor drill bit 113. The drill guide 104 includes an insert portion 104a, a main body 104b, and a guide portion 104c.

The insert portion 104a includes an elongate member that conforms to dimensions of a bone hole. The insert portion 104a as shown is an elongate member that is dimensioned to slidably fit within a primary hole 118 and be held firmly within the primary hole relative to the bone. At a free end of the insert portion 104a is a pointed edge or inverted cone shape that is dimensioned to conform with an end of a pre-drilled hole 118. The shape of the end of the hole 118 may be any shape such as that shown of an end of a drill bit. Alternatively, the free end of the insert portion 104a may be flat or have another shape as desired.

The main body 104b of the drill guide 104 includes a member that adjoins the insert portion 104a and the guide portion 104c. The main body 104b is angled, bent, or curved to angle the insert portion 104a relative to the guide portion 104c. The main body 104b as shown is curved in the shape of an arc. The thickness or diameter of the main body 104b is dimensioned to allow a manual grip of a standard anatomical person, such as that used for medical equipment, manual equipment, or professional gloves, etc.

The guide portion 104c of the drill guide 104 includes a cylindrical or a slightly tapered conical body as shown that is hollowed therethrough to allow a drill bit 113 or other member to be slidably, removably inserted and directed to drill an anchor hole (not shown) in the bone 108.

The relative angle between the insert portion 104a and the guide portion 104c includes an angle range of one or more of 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 150-155, 155-160, 160-165, and 165-170 degrees. The relative angle shown is 90 degrees. The subsequent angle between the holes that are drilled correspond to the angles listed.

Figure 4:
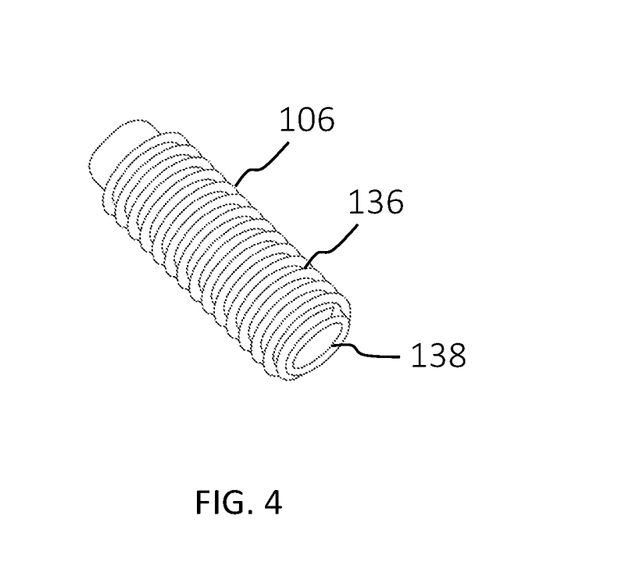
FIG. 4 illustrates a perspective view of a cannulated device.

FIG. 4 illustrates a cannulated device 106. The cannulated device 106 shown is an anchor member that includes a generally elongated cylindrical body having an axial cylindrical channel 138 extending therethrough. An exterior surface of the cylindrical body includes threads 136 to engage inner walls of the anchor hole 116 with a screw type fit. As shown, the outer threads are recessed more than a pitch of the outer threads away from a deep end of the cannulated device to provide a space from the corner or curved portion. Other types of fit are anticipated, such as a friction fit and slide fit with locking structure. Also, the exterior may be smooth or have a rough surface.

Figure 5:
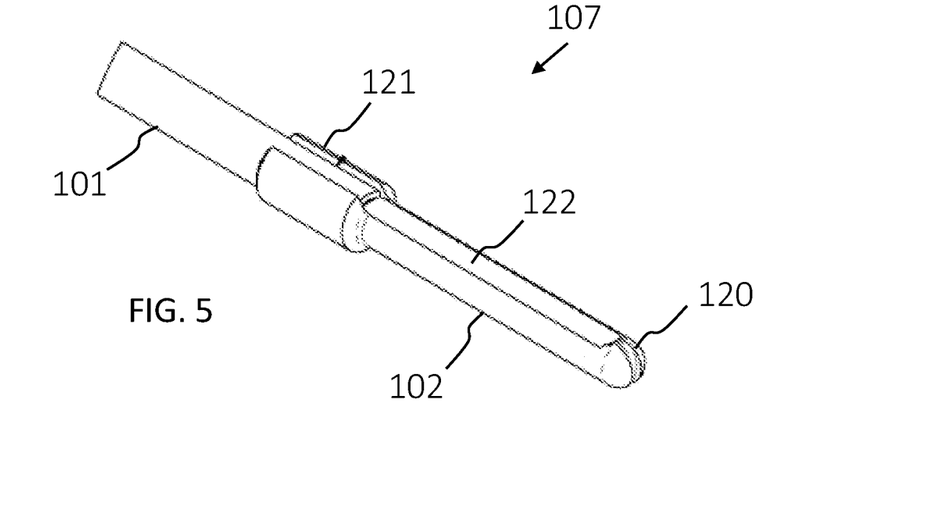
FIG. 5 illustrates a perspective view of a working end.

FIG. 5 illustrates a perspective view of a working end 102 of a suture passer 107. The working end 102 is a straight, elongate member having a blunted, rounded tip at an end of the elongate member. The working end includes an opening on one side at the end of the elongate member. A curved surface at the end of the elongate member is to direct suture within the bone tunnel around the corner or curved portion. The working end 102 is to handle passage of suture through a bone tunnel. At one end of the working end 102 is a rounded, blunt tip 120. The bottom end curves upward to form a peak or curved tip that extends relatively upward. The top of the tip also curves upward to join the bottom tip and define the peak. An overall curvature from the bottom to the top may guide suture through a directional change of one or more of 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 150-155, 155-160, 160-165, and 165-170 degrees. The curved tip 120 is advantageous because it does not have sharp edges that would otherwise contact inner walls of a bone tunnel, potentially damaging them or even cutting them.

The proximal end of the working end 102 may be a single piece with the delivery driver.

Alternatively, the working end 102 may be removably attached to a delivery driver 134. For example, there may be an attachment 121 on the proximal end for attachment to a delivery driver 134 as shown. The exemplary attachment 121 shown includes an outer shaft that fits around a delivery shaft 101 of a delivery driver 134 and which includes a locking or tightening structure for securement.

The cavity 122 of the working end 102 extends into a shaft within the attachment 121, the fit between the outer shaft 121 and delivery shaft 101 being a snap fit, screw fit, or any other type of fit known in the art. The connection may be permanently fixed or removable to allow other assemblies with a given delivery driver.

Figure 6:
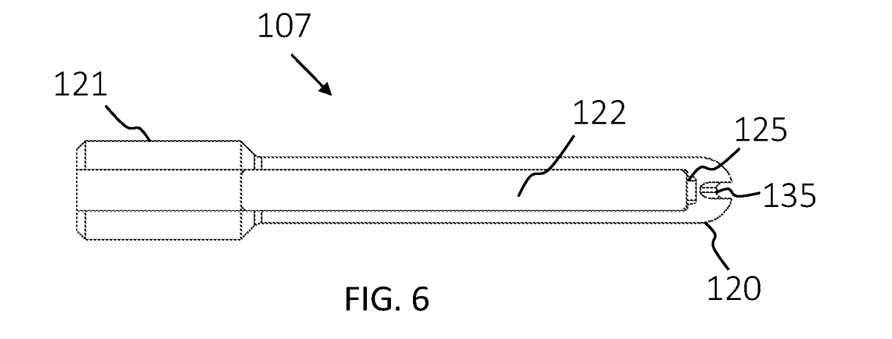
FIG. 6 illustrates a top view of a working end.

FIG. 6 illustrates a top view of the working end which clearly shows the elongate cavity 122 being centrally located on top of the suture passer 102 and which extends from one end of the suture passer 102 to another and and is dimensioned to allow a micro cover fitting to be placed over the elongate cavity 122.

Figure 7:
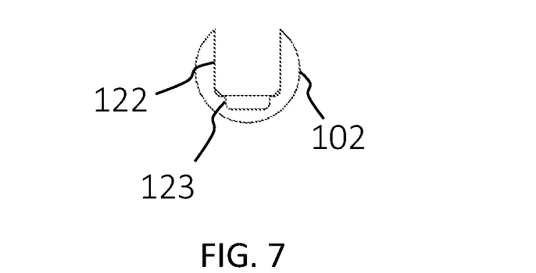
FIG. 7 illustrates a cross-section of a front view of a working end.

FIG. 7 illustrates a front view of a cross section of the working end 102. The cavity 122 is shown having a rectangular cross-sectional shape, however, other shapes are anticipated including square, oval, circle, triangle, etc. Edges of the cavity 122 may be slightly rounded to avoid sharp corners. Below the cavity is a sub-cavity 123 in which a slider 141 is to be passed therethrough. The sub-cavity 123 is an elongate hollow that runs through the working end in parallel with the cavity 122. Interior walls of the sub-cavity 123 allow the slider 141 to be nested within the sub-cavity 123 and smoothly slide from one end to another. The sub-cavity 123 is an elongated space that curves at the distal end to provide a curved path for one or more of a slider to be pushed through a bone tunnel. Exit space 125 is described below in relation to FIG. 9.

A notch 135 may be present at the tip of the working end. The notch 135 includes a centrally located divot that runs from the top of the tip to the bottom of the tip. The base of the notch is rounded forming a U-shape. The notch guides suture to be passed from underneath the working end 102 to a top of the tip of the working end.

Figure 8:
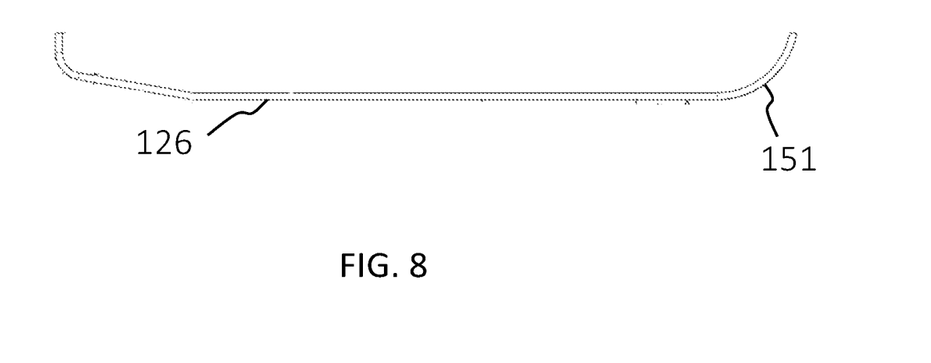
FIG. 8 illustrates a side view of a micro cover fitting.
Figure 9:
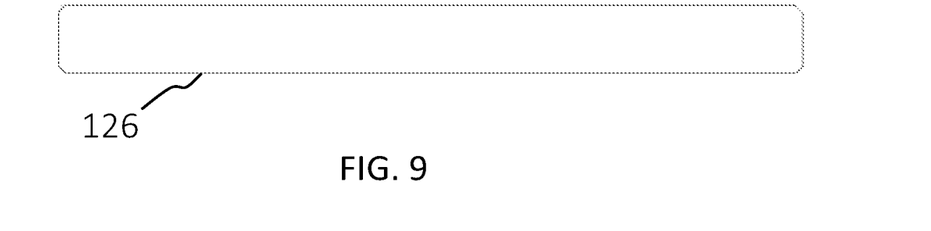
FIG. 9 illustrates a top view of a micro cover fitting.

FIG. 8 shows a side view of a micro cover fitting 126 which includes a curved or rounded tip 151 to conform with the tip 120 of the working end 102. The angle of curvature may be the same or different as the angle of curvature of the suture passer 102. A top view of the micro cover fitting 126 as shown in FIG. 9 includes a rectangular shape.

Turning back to FIG. 6, a tip of the cover 126 stops short at a length prior to the end of the cavity 122 to define an exit space 125 to allow space for the slider 141 to exit from the cavity 122. The exit space 125 between the end of the cover and the end of the cavity may have a rectangular shape from a top view perspective as shown. Alternatively, the shape may have other shapes as listed above for the cavity. The exit space 125 is dimensioned for at least one slider 141 to pass from the suture passer 102 to an external environment.

Figure 10:
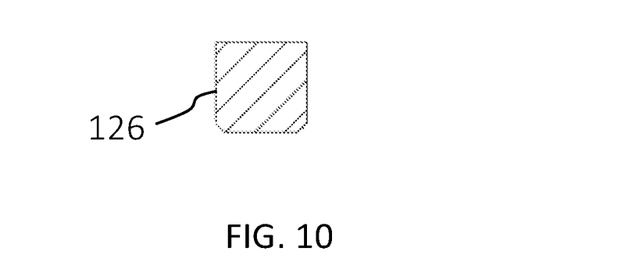
FIG. 10 illustrates a cross-section of a front view of a micro cover fitting.

FIG. 10 shows a cross section of a front view of the micro cover fitting 126 to be generally square in shape, however, other shapes described above are anticipated. At the opposite end of the tip 151 of the micro cover fitting 126 is a free end that may be attached to one or more of the delivery shaft 101 and the outer shaft 121 of the suture passer 102. The micro cover fitting 126 may be attached with a friction fit, snap fit, welded, or locking structure.

Figure 11:
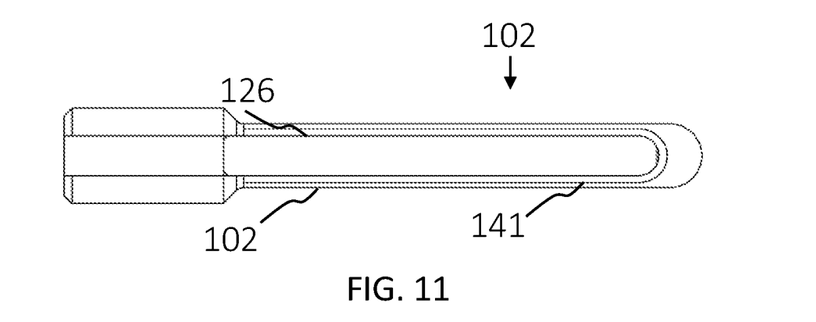
FIG. 11 illustrates a top view of a working end with a micro cover fitting.

The micro cover fitting 126 may or may not be used with the suture passer 102. Turning to FIG. 11, the working end 102 is shown with the micro cover fitting 126 which extends along the length of the cavity 122. Also shown is a slider 141. In use, the suture is threaded through a loop of a slider or otherwise secured so that movement of the slider as caused by a delivery driver or other means causes the suture to follow the movement of the slider. The slider is moved along the length of the sub-cavity 123 and the suture is moved underneath or otherwise by the working end 102. At the tip of the working end 102 shown, the slider 141 exits through the exit space 125. The slider 141 is then pushed through the primary hole while the suture 112 is pulled by the slider 141 through the primary hole.

Figure 12:
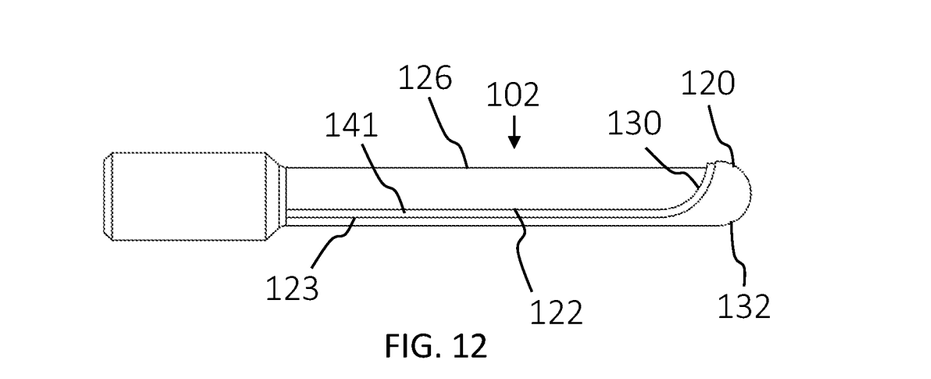
FIG. 12 illustrates a cross-section of a side view of a micro cover fitting and working end.

A side view of the working end 102 is shown in FIG. 12. A slider 141 is located beneath the micro cover fitting 126 in the sub-cavity 123 and runs parallel along the length of the micro cover fitting 126 and working end 102. The slider 141 is a generally flat elongated strip and includes properties to pass suture through the bone tunnel. For example, the slider 141 may comprise nitinol, a nickel-titanium alloy. The slider may also comprise other types of metal alloys that are distinguished by having shape memory and super-elastic characteristics. Any material with characteristics like a spring-like steel are anticipated. This characteristic is advantageous because the slider can be pushed and pulled and still maintain its original shape.

Figure 13:
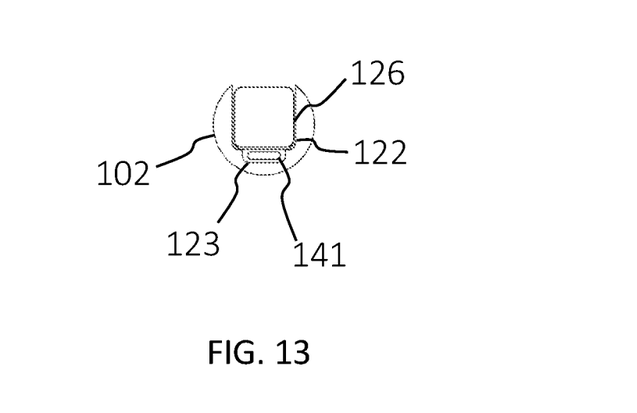
FIG. 13 illustrates a cross-section of a front view of a working end, micro cover fitting, and a suture passer.

Turning to FIG. 13, a cross-sectional view of the front of the working end is shown with the micro cover fitting 126 and the slider 141. The micro cover fitting 126 has a square cross-sectional shape, its edges extending past edges of the cavity 122 to completely cover the cavity. Sidewalls of the cavity 122 define top surfaces that serve as inner shoulders for edges of the cover 126 to be placed against. The sub-cavity 123 is recessed within a bottom surface of the cavity 122 and has smaller dimensions for the slider 141. Corners between inner sidewalls of the sub-cavity 123 and top surfaces of the sidewalls of the cavity 122 may be slightly rounded. Also, corners between sidewalls of the sub-cavity 123 and a bottom surface of the sub-cavity 123 may be slightly rounded. Sharp corners are also anticipated. The fit of the micro cover fitting 126 within the suture passer 102 may be a friction fit or a slidable fit. Instead of a square shape, the micro cover fitting 126 may have other shapes as listed above for the cavity.

An exemplary delivery driver for the suture passer includes a gun 134 with a trigger as shown in FIGS. 14 and 15. The gun 134 allows the working end 102 and cover 126 to be attached to a delivery shaft 101 of the gun 134. The gun 134 and the working end 102 may not require any attachments however and be a solid piece with no fittings required.

Other types of delivery drivers are anticipated, including for example, simple handles, assembly, thumb wheel, shuttle suture (loading the suture after the fact), and mechanical devices with other types of handles than a trigger.

Figure 16:
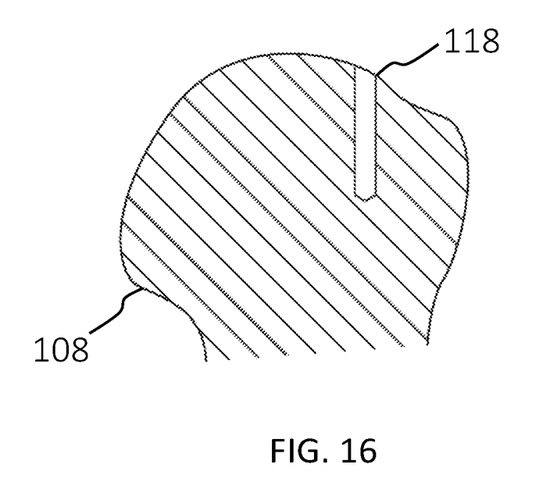
FIG. 16 illustrates a cross-section of a front view of a primary hole drilled into a bone.

The method of use for the surgical kit will now be described according to examples and principles described herein. Turning to FIG. 16, a primary hole 118 has been drilled in bone 108. The hole is of sufficient depth and diameter and form to allow an insert portion 104a of the drill guide 104 to be inserted and held fixed to provide positioning for the anchor hole 116 to be drilled relative to the primary hole.

Figure 17:
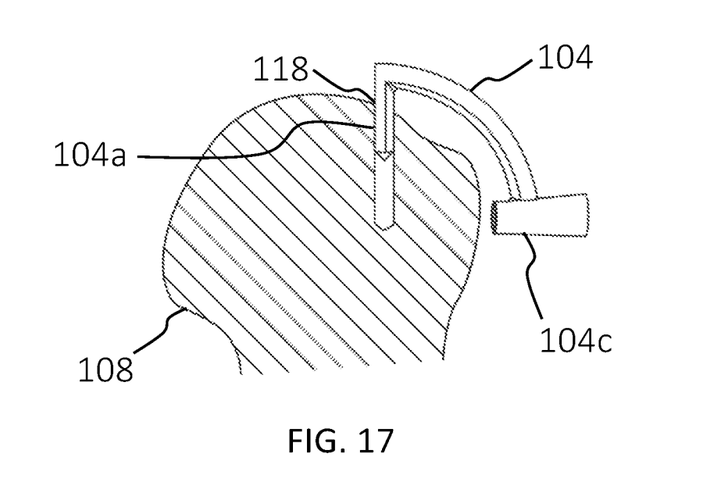
FIG. 17 illustrates a cross-section of a front view of a drill guide inserted into a primary hole of a bone.

As seen in FIG. 17, the insert portion 104a is received within the primary hole 118 and lowered within the hole to a depth in which the guide portion 104c of the drill guide 104 is to be aimed at the bottom of the primary hole 118. The depth of the insert portion 104a can be adjusted as desired. The diameter of the guide portion 104c is dimensioned to allow for fitment within the anchor hole 116 of one or more of a cannulated device, a working end, and a cannulated device inserted around the outer diameter of the working end.

The primary and anchor holes may be made with a drill bit, or other structure or device. The anchor hole 116, like the primary hole 118, may have a pointed edge or inverted cone shape that is dimensioned to conform with an end of a pre-drilled hole. The shape of the end of the hole 116 may be any shape such as that shown of an end of a drill bit. Alternatively, the end of the anchor hole may be flat or have another shape as desired.

The primary 118 and anchor holes 116 are to intersect and thus form a bone tunnel, the point of intersection forming a corner within the bone tunnel. The two holes may be of similar or different dimensions. For example, the holes may have similar or different lengths and diameters. One or more of the holes may extend past each other.

Figure 18:
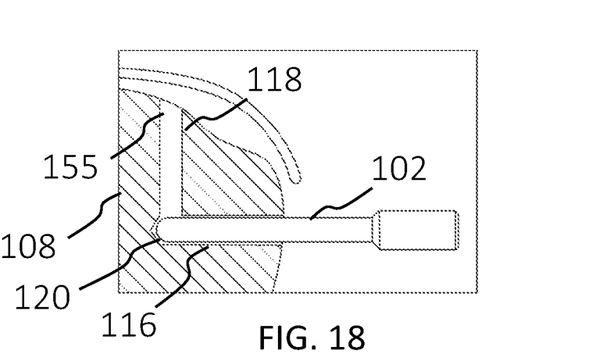
FIG. 18 illustrates a cross-section of a front view of a working end inserted into an anchor hole of a bone.
Figure 19:
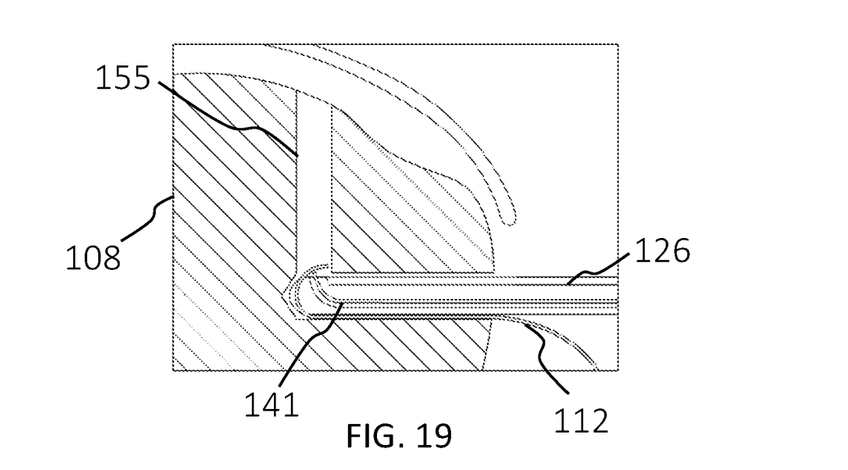
FIG. 19 illustrates a cross-section of a front view of a working end passing suture through an anchor hole of a bone.

As shown in FIGS. 18 and 19, the primary 118 and anchor holes 116 are located perpendicular to each other forming bone tunnel 155 with a 90 degree angle. Other angles are contemplated including a 10-15, 15-20, 20-25, 25-30, 30-35, 35-40, 40-45, 45-50, 50-55, 55-60, 60-65, 65-70, 70-75, 75-80, 80-85, and 85-90 degree relative angle. The angle of the tunnel bend may vary according to the angle of the drill guide 104 or formation of the two holes by some other means.

In FIGS. 18 and 19, the working end 102 is inserted within the anchor hole 116. In FIG. 19, suture 112 is shown running along the bottom of the working end 102. An end of the suture 112 has a knotted loop attached to a hook end of the slider 141 so as to be guided through the bone tunnel 155. The suture passer 102 is shown inserted into the anchor hole 116 until the tip 120 of the working end 102 reaches the end of the anchor hole 116 or the corner formed between the anchor hole 116 and the primary hole 118. Suture 112 is pulled by the slider 141 through the working end 102, through the tunnel 155.

The micro cover fitting 126 is shown covering the cavity 122. The micro cover fitting 126 has a flat underside which provides a flat surface for the slider 141 to slide between the micro cover fitting 126 and the cavity 122. The micro cover fitting 126 is not required for the slider 141 to still slide within the cavity 122 but is a feature that may be used if desired.

The curvature of the tip 120 of the working end 102 directs the suture 112 to curve upward toward the top of the bone tunnel 155 as it works its way through the bone tunnel 155. The curvature prevents the suture 112 from bending at a sharp angle which could weaken the suture 112. The curvature further directs the suture 112 away from any sharp corners in the bend of the bone tunnel 155 which could weaken or cut the suture 112. Note that the micro cover fitting 126 may have a rounded tip to prevent the suture from being cut on its top surface. The working end 102 provides insertion of suture while protecting the suture 112 against contact with surfaces of the bone tunnel. The blunt edge of the tip 120 is not sharp against corners and surfaces within the bone tunnel 155.

Figure 20:
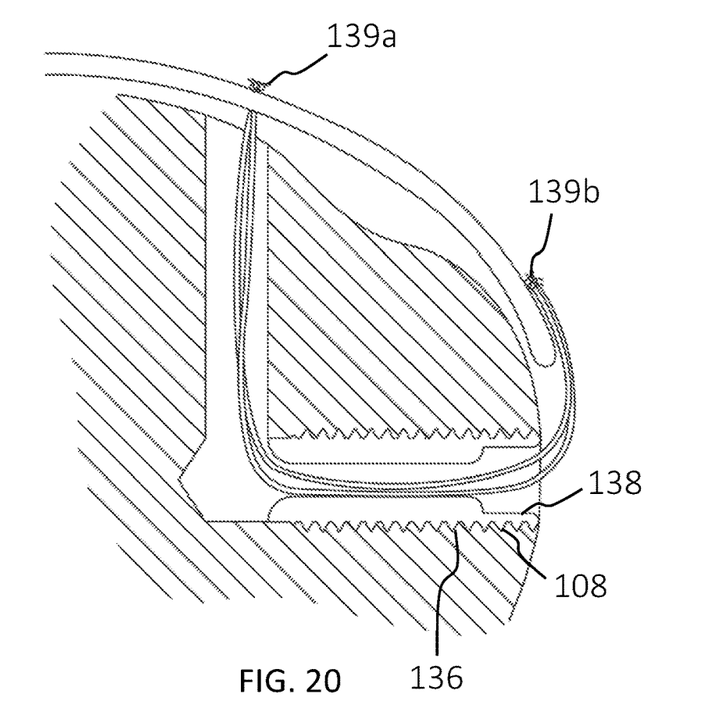
FIG. 20 illustrates a cross-section of a front view of a dynamic tendon fixation.
Figure 21:
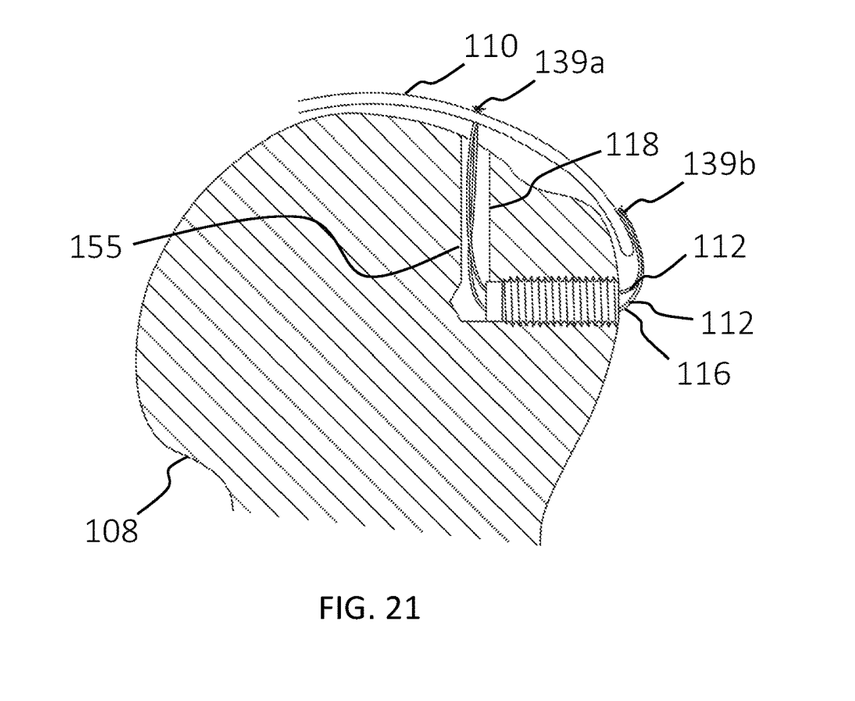
FIG. 21 illustrates a cross-section of a front view of a dynamic tendon fixation.

Turning to FIGS. 20 and 21, cross-sectional side views of completed Modified Mason-Allen fixation are shown. Suture is fixated at fixation points 139a and 139b and has a dynamic fit through a cannulated device 106. The cannulated device 106 is positioned inside the anchor hole 116. Outer screw threads 136 of the cannulated device 106 provide for a screw type fit within the bone tunnel. Other types of fit are anticipated such as a friction fit or structure locking fit.

Note that the suture 112 may be passed in different ways, for example, the suture 112 may be passed under, on top of, or through the suture passer 102 and through the bone tunnel 155. This process may be accomplished with the use of a slider or with any kind of suture passing mechanism. Using a desired device or a method of passing the suture, the suture is directed through the primary hole 118 by way of the anchor hole 116 and the corner or bend of the bone tunnel 155. The suture 112 exits through the exit space 125 and up through the primary hole.

Tensile forces exerted by the distal end of the tendon 110 are communicated through the suture 112 to the more proximal fixation point 139a to convert the tensile forces between fixation points 139a and 139b to be compressive forces against the bone 108, particularly over the TTC region. The channel 138 within the cannulated device 106 allows the suture 112 to be slidably engaged so that there is a dynamic compressive force against the bone 108 from within the cannulated device. The cannulated device 106, like the working end 102, directs the suture 112 so as to not cut the bone as it is passed or contained within the bone tunnel 155.

Figure 22:
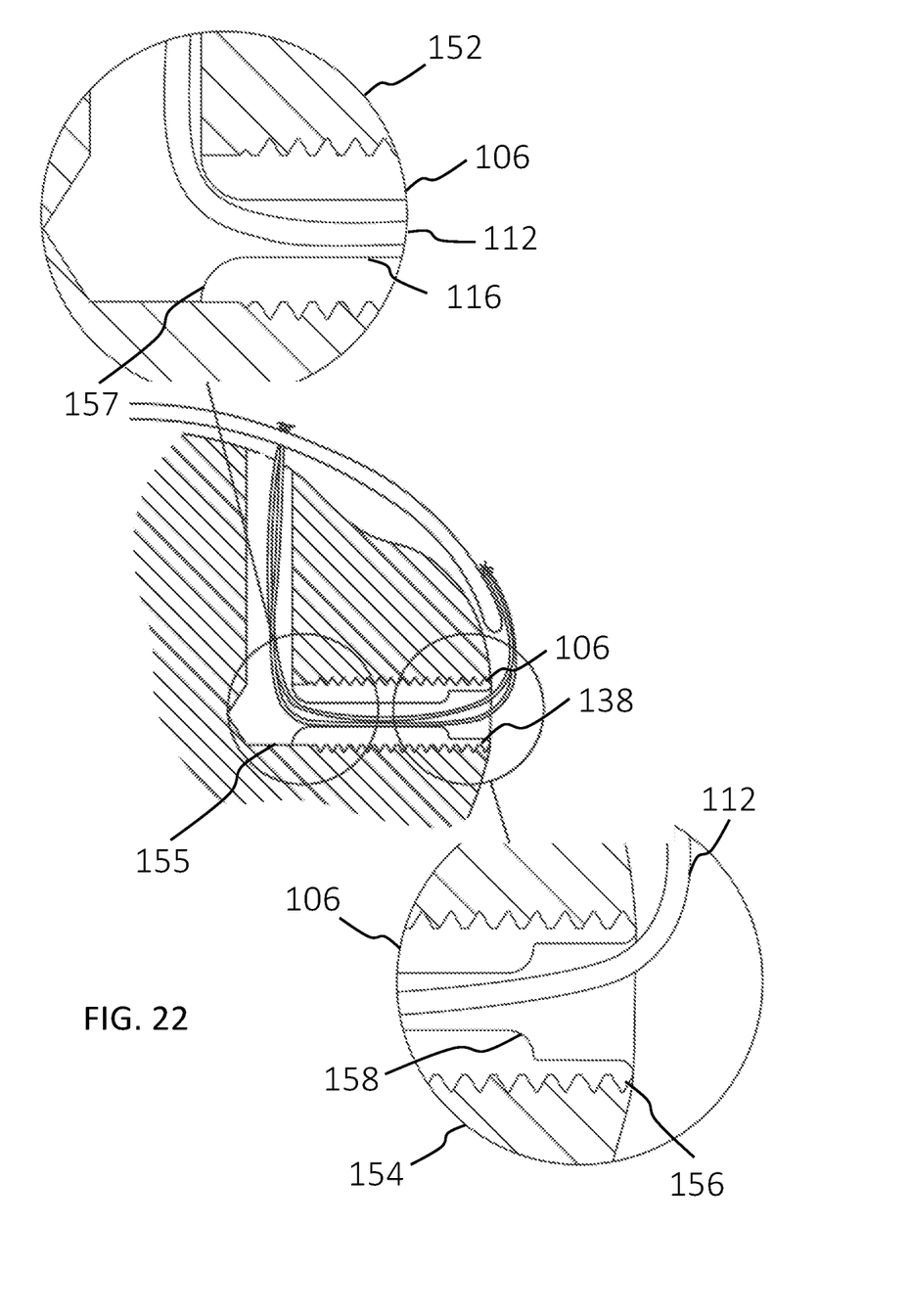
FIG. 22 illustrates a cross-section of a front view of a dynamic tendon fixation and a close-up cross-sectional view of each of the end portions of a cannulated device.

FIG. 22 illustrates two cross-sectional close-up views of portions, a deep portion 157 and a superficial portion 156, of the bone where the cannulated device 106 is located. The deep portion 157 where the cannulated device 106 is located shows that the opening of the channel 138 at the deep end is defined by sidewalls that curve outward and extend away from the opening at the deep end. This allows the suture 112 to dynamically glide through the cannulated device 106 without being cut by sharp corners. This also allows the suture 112 to pass around a curve rather than engage with an acute corner. Another advantage is that it keeps the suture centrally located as it travels within the bone tunnel.

The other close-up view is of the superficial portion 156 where the cannulated device 106 is located. The superficial portion is defined by an end section having a larger diameter channel than a diameter of the main portion of the channel 138. The end section may conform to dimensions of a screwdriver or other device that is used to insert the cannulated device 106 within the bone tunnel 155. Sidewalls that define the end section curve outward to form a rounded shoulder 158 at the intersection of the main portion and the end section. The sidewalls also provide curvature at the opening of the superficial side.

Variations include a channel within the cannulated device 106 that has a constant diameter throughout and no portion with a larger diameter.

Surgeons can keep using protocols they are familiar with to implement principles discussed herein. For example, suture passers and cannulated devices may still be used in the same or similar manner.

In an exemplary procedure, a slider 141 is placed within the sub-cavity 123 of the working end 102. Suture 112 is secured to the slider 141, for example, the suture 112 may run underneath the working end 102 and a free end of the suture 112 may have a knotted loop that is attached to a hook end of the slider 141 as shown in FIG. 19. The working end 102 including slider 141 and suture are inserted within the anchor hole 116. The slider 141 is pushed off the rounded curved tip of the suture passer 102 and around the corner of the bone tunnel 115 and directed out of the primary hole 118 of the bone tunnel 155. The suture 112 follows the course of the slider 141 as it slides underneath the working end 102 and around the notch 124 on the tip of the working end 102. The suture is directed through the bone tunnel and out through the opening of the primary hole 118. The working end 102 and the slider 141 are removed but the suture is left inside the bone tunnel 155 with free ends sticking out of the two openings. The free end of the suture 112 sticking out of the anchor hole 116 enters a channel 138 of a cannulated device 206 as the cannulated device 206 is inserted within the anchor hole 116. If the cannulated device 206 is threaded, a screw fit entry is performed. The free ends of the suture are then tied to the tendon 110 at fixation points.

In another example, the cannulated device 106 is inserted within the anchor hole 116 first. Then, the working end 102 including the suture 112 and slider 141 is inserted within a channel 138 of the cannulated device 106. The channel 138 of the cannulated device 106 in this example is dimensioned to receive a working end 102. The suture 112 is directed through the bone tunnel 155 by the slider 141. Then, the working end 102 is removed from the cannulated device 206 and the cannulated device 206 remains in place. The free ends of the suture 112 can then be tied to the tendon 110 at fixation points.

In another example, the cannulated device 106 is inserted together with the working end 102 and suture 112 and slider 141. The slider 141 directs the suture 112 out of the bone tunnel 155 and then the working end 102 is removed so that the free ends of the suture 112 can be tied to the tendon 110 at fixation points.

Figure 23:
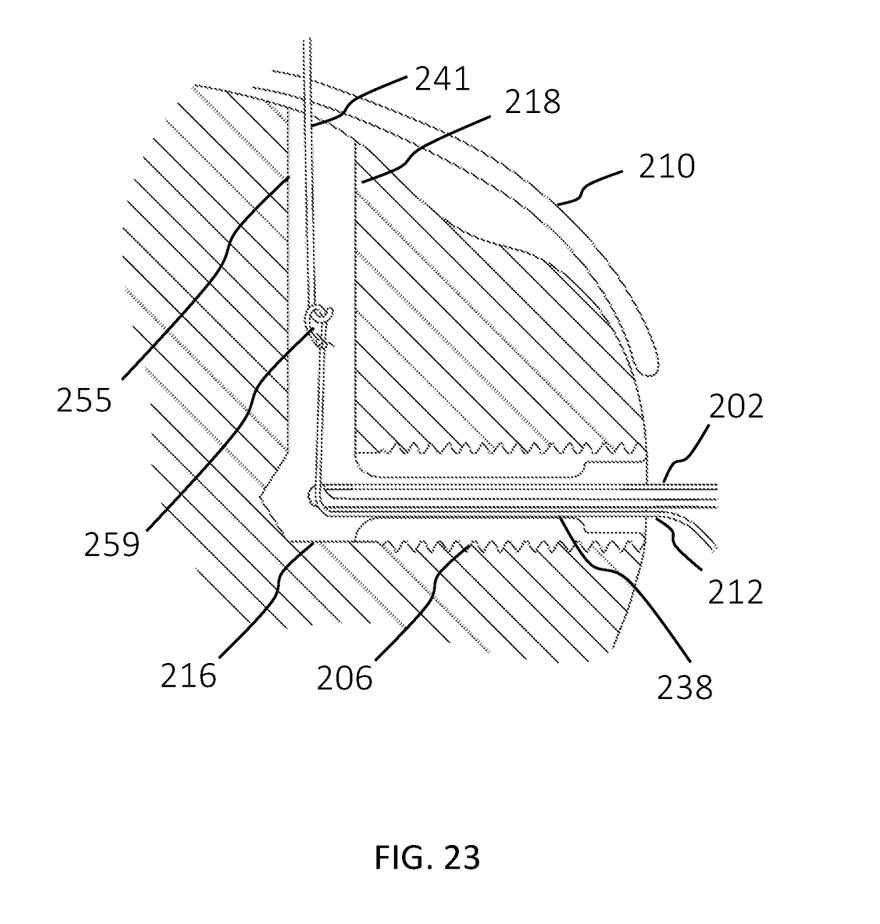
FIG. 23 illustrates a cross-section of a front view of a working end passing suture through a cannulated device in an anchor hole of a bone.

FIG. 23 illustrates a cross-sectional view of a cannulated device 206 and a working end 202 together inserted within the anchor hole 216. The cannulated device 206 is screwed into the anchor hole 216. The working end 202 is then slidably inserted within the channel 238 of the cannulated device 206. Instead of being done one at a time, the cannulated device 206 and the working end 202 may be inserted within the anchor hole 216 together at the same time. Suture 212 is inserted alongside the working end 202 within the anchor hole 216 either before or after the working end 202 is placed within the anchor hole 216. The suture 212 has a knotted loop or other configuration at a free end.

Once the working end 202 and the cannulated device 206 are placed within the anchor hole 216, a slider 241 is inserted through the primary hole 218 until an end portion of the slider 241 grabs the knotted loop of the suture 212 to thereby pull the suture 212 through the bone tunnel 255 and exit through the primary hole 218. The working end 202 is then removed while the cannulated device 206 remains within the bone tunnel 255. Free ends of the suture 212 can then be tied to the tendon 210 at fixation points. Alternatives include that both the cannulated device 206 and the working end 202 be removed for securement of the suture 212 to tendon 210.

Figure 24:
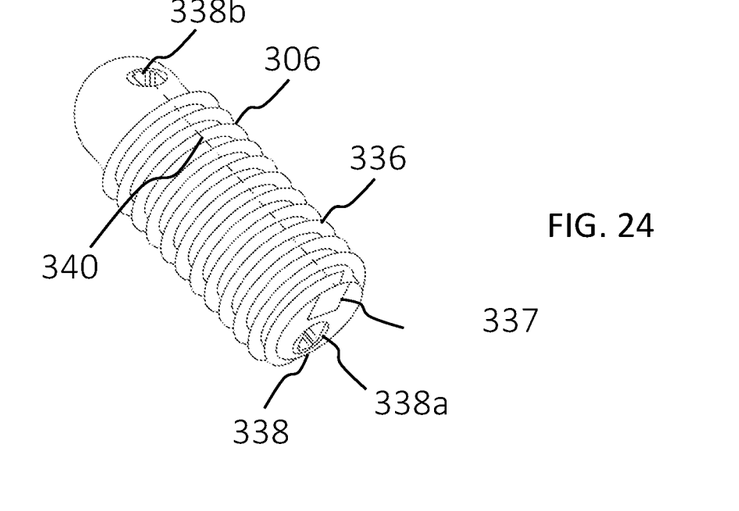
FIG. 24 illustrates a perspective view of a cannulated device.
Figure 25:
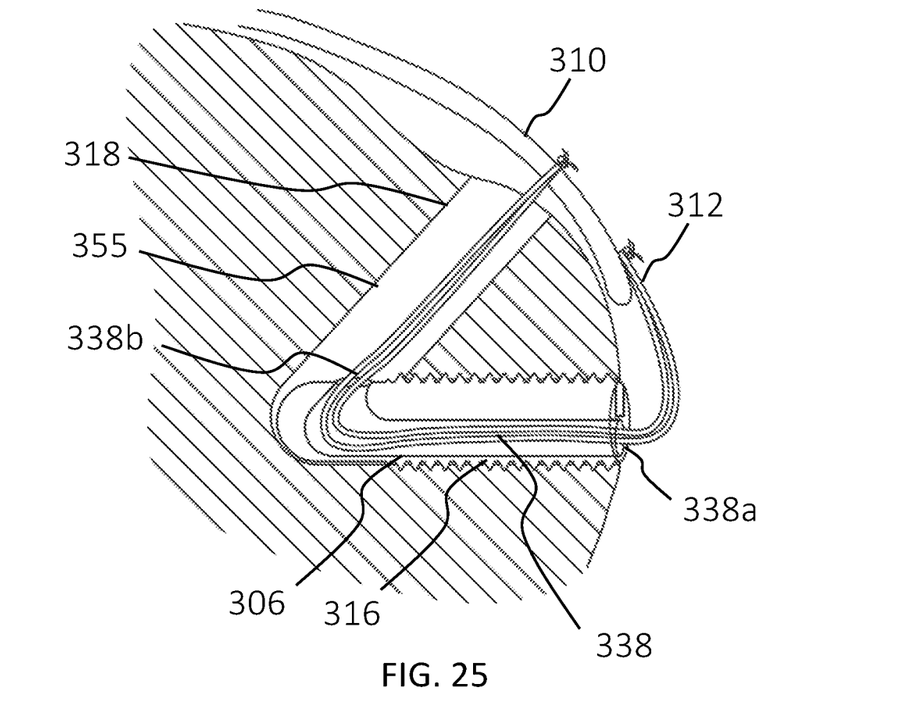
FIG. 25 illustrates a cross-section of a front view of a dynamic tendon fixation.

Instead of a channel running axially straight through a cannulated device, the channel may incorporate a bend within the cannulated device to thereby direct suture around a corner or bend of a bone tunnel. Turning to FIGS. 24 and 25, this variation is shown with a cannulated device 306 that includes an elongated cylindrical member having a channel 338 that runs therethrough. The channel 338 includes a proximal opening 338a located at or near a proximal end of the cylindrical member. The proximal opening 338a may be in alignment with a central axis of the cylindrical member, or may be offset from the central axis as shown. The cylindrical member further includes a distal opening 338b of the channel 338 located on an exterior surface of the cylindrical member at or near a distal end of the cylindrical member.

Because the proximal opening 338a and distal opening 338b are not axially aligned, an alignment structure or indicator may be included with the cannulated device 306. As shown, an index marking 337 is located at a proximal end of the cannulated device 306 and includes a visible mark to indicate a physical relationship between the proximal opening 338a and the distal opening 338b. Particularly, the index marking 337 indicates alignment of the index marking 337 and the distal opening 338b of the channel 338. The alignment is illustrated with a dotted line 340 that runs from the index marking 337 and the distal opening 338b. Variations of the index marking 337 include a raised surface structure, color, etching, demarcation, or other type of mark that may be used to communicate alignment.

FIG. 25 illustrates a cross section of a completed modified Mason-Allen fixation using the cannulated device 306. The channel 338 of the cannulated device 306 as shown runs co-axially along the length of the elongated member from the proximal opening 338a and bends at or near the distal end of the elongated member. At or near the surface exterior and after making the bend is the distal opening 338b. The bend provides a natural curvature or bend to the suture 312 within the bone tunnel. Corners at the bend may be rounded so as to avoid cutting into the suture 312.

The angle at the bend may be 0-25 degrees, 25-50 degrees, 50-75 degrees, 75-100 degrees, 100-125 degrees, 125-150 degrees, or 150-180 degrees. The bend of the channel 338 may be used to adapt to various bone tunnels. As illustrated, the bone tunnel 355 includes a 45 degree bend relative to the anchor hole 316. The bend directs the channel 338 to be at or near alignment with the primary hole 318.

In practice, the cannulated device 306 is inserted within the anchor hole 316 with a screw fit. Rotation of the cannulated device 306 within the anchor hole can be adjusted and fine-tuned based on the index marking 337 to obtain alignment of the distal opening 338b with the primary hole 318.

Suture 312 is directed through the channel 338 by a slider or other means and free ends of the suture 312 are fixated to tendon 310. The cannulated device 306 may be advantageous in that it can be used without requiring a slider to be inserted within the channel 338. The bended channel 338 already directs suture around a corner of a bone tunnel. A slider is then passed through the primary hole to connect with a free end of suture and pass the suture through the primary hole.

Note that principles from the examples can be used to incorporate a plurality of sutures. Other techniques may be used with the surgical kit and the examples described are in no way to be limiting.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:
1. A method of forming a tendon fixation comprising:
   forming a bone tunnel that has a corner or a curved portion wherein forming the bone tunnel comprises:
   forming a primary hole within a bone;
   inserting an insert portion of a drill guide into the primary hole;
   maintaining the drill guide in a stationary position relative to the bone to provide orientation relative to the bone;
   drilling an anchor hole into the bone as directed by a hollow shaft of a guide portion of the drill guide, the anchor hole intersecting the primary hole;
   inserting a working end within an anchor hole of the bone tunnel, the working end having a straight, elongate member with a blunted, rounded tip at an end of the elongate member, the working end further having an opening on one side of the elongate member and a curved surface at the end of the elongate member;

passing suture along the curved surface and out of the opening of the working end to direct the suture around the corner or curved portion, the suture having a first and second end;

inserting and fixating a cannulated device within the bone tunnel, the cannulated device having outer threads to fixate the cannulated device to inner walls of the bone tunnel;

receiving the suture through a straight channel of the cannulated device, the channel having a circular cross section and being centrally located within the cannulated device to direct the suture along a straight path through the bone tunnel, opposite end openings having inner sidewalls that curve outward to direct the suture in a curved path at the end openings and thus avoid contact with the corner or the curved portion of the bone tunnel; and stitching the first and second ends of the suture that extend from openings of the bone tunnel at different fixation points of the tendon to provide a dynamic suture fixation that yields a compressive force on the bone.

2. The method of claim 1, wherein the insert portion and the guide portion are oriented at a 90 degree angle relative to each other.

3. The method of claim 1, wherein the working end includes a blunt, rounded tip whereby the suture curves around the tip to be directed through a corner of the bone tunnel.

4. The method of claim 1, further comprising moving suture through the bone tunnel with a slider.

5. The method of claim 4, wherein the slider moves within a cavity of the working end.

6. The method of claim 1, wherein the working end is removable from a delivery driver.

7. The method of claim 1, further comprising a micro cover fitting that is removably attached over a cavity of the working end.

8. The method of claim 1, further comprising, tying ends of the suture using one or more of a Mason-Allen fixation.

9. A method of forming a tendon fixation comprising:
forming a bone tunnel with an instrument so that the bone tunnel has a corner or a curved portion, wherein forming the bone tunnel comprises:
forming a primary hole within a bone;
inserting an insert portion of a drill guide into the primary hole;
maintaining the drill guide in a stationary position relative to the bone to provide orientation relative to the bone; and
drilling an anchor hole into the bone as directed by a hollow shaft of a guide portion of the drill guide, the anchor hole intersecting the primary hole;

passing suture through the bone tunnel, comprising:
inserting a working end within a hole of the bone tunnel, the working end having a straight, elongate member with a blunted, rounded tip at an end of the elongate member, the working end further having an elongate opening on one side at the end of the elongate member, a curved surface at the end of the elongate member to direct suture within the bone tunnel around the corner or curved portion;

passing suture by the working device through the bone tunnel, the suture having a first and second end;

inserting and fixating a cannulated device within the portion of the bone tunnel, the cannulated device having outer threads to fixate the cannulated device to the bone tunnel, the outer threads recessed more than a pitch of the outer threads away from a deep end of the cannulated device to provide a space from the corner or curved portion, the cannulated device having a straight channel with a circular cross section to provide a straight path for suture to pass through, the cannulated device having a deep end opening with a first diameter and a superficial end opening having an end section with a larger diameter channel than the deep end opening, the larger diameter channel dimensioned for a driving device to insert the cannulated device into the bone tunnel, both the deep end opening and the superficial end openings having inner sidewalls that curve outward to direct the suture in a curved path at the deep and superficial end openings;

receiving the suture through the channel of the cannulated device, the first and second end of the suture that extend from respective openings of the bone tunnel to be secured at different fixation points of the tendon, a region to be bounded between the two fixation points such that a tensile force on the tendon communicates a compressive force through the suture with the suture having a dynamic sliding engagement within the bone tunnel; and fixating the suture, comprising:
stitching the first and second ends of the suture that extend from openings of the bone tunnel at different fixation points of the tendon to provide a dynamic suture fixation that yields a compressive force on the bone.

* * * * *